US010708234B2

(12) United States Patent
Adams et al.

(10) Patent No.: US 10,708,234 B2
(45) Date of Patent: Jul. 7, 2020

(54) SYSTEM, METHOD, AND RECORDING MEDIUM FOR PREVENTING BACK PROPOGATION OF DATA PROTECTION

(71) Applicant: International Business Machines Corporation, Armonk, NY (US)

(72) Inventors: Samuel Scott Adams, Rutherfordton, NC (US); Susann Marie Keohane, Austin, TX (US); James R. Kraemer, Santa Fe, NM (US); Jeb R. Linton, Manassas, VA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 508 days.

(21) Appl. No.: 15/079,203

(22) Filed: Mar. 24, 2016

(65) Prior Publication Data

US 2017/0277904 A1  Sep. 28, 2017

(51) Int. Cl.
*G06F 21/00* (2013.01)
*H04L 29/06* (2006.01)
(Continued)

(52) U.S. Cl.
CPC ........ *H04L 63/0421* (2013.01); *G06F 21/606* (2013.01); *G06F 21/6263* (2013.01); *H04L 9/3218* (2013.01); *G16H 10/60* (2018.01)

(58) Field of Classification Search
CPC .............. G06F 21/6218; G06F 21/606; G06F 21/6263; H04L 63/0421; H04L 9/3218; G16H 10/60
See application file for complete search history.

(56) References Cited

U.S. PATENT DOCUMENTS 8,166,406 B1 * 4/2012 Goldfeder ........... G06F 21/6263
709/224
2014/0337090 A1 * 11/2014 Tavares .............. G06Q 30/0201
705/7.29

FOREIGN PATENT DOCUMENTS

WO WO 2015/148693 A1 10/2015
WO WO-2019132645 A1 * 7/2019 ........... H04L 9/0836

OTHER PUBLICATIONS

Wei Chang, Jie Wu; "Strengthening data privacy during propagation"; SPME '14: Proceedings of the ACM MobiCom workshop on security and privacy in mobile environments; Sep. 2014; pp. 37-42 (Year: 2014).*

(Continued)

*Primary Examiner* — Shewaye Gelagay
*Assistant Examiner* — Courtney D Fields
(74) *Attorney, Agent, or Firm* — Anthony R. Curro, Esq.; McGinn IP Law Group, PLLC

(57) ABSTRACT

A third party intermediary and a data protection method, system, and non-transitory computer readable medium, include a content request receiving circuit configured to receive a service request from a user, to communicate the service request to a provider, and to receive pre-approved versions of content from the provider, a content matching circuit configured to match a pre-approved version of content of the pre-approved versions of content to the user based on a condition of the user, a user data receiving circuit configured to receive user data to complete the pre-approved version of the content, and a zero-knowledge verifiable computing circuit configured to execute a program using zero-knowledge verifiable computing to remove private content from the pre-approved version of the content to ensure privacy of the condition of the user from the provider.

18 Claims, 6 Drawing Sheets

(51) Int. Cl.
*H04L 9/32* (2006.01)
*G06F 21/60* (2013.01)
*G06F 21/62* (2013.01)
*H04L 9/08* (2006.01)
*G16H 10/60* (2018.01)

(56) References Cited

OTHER PUBLICATIONS

Kaingade, RM. et al.; "Personalization of Web search based on privacy protected and auto-constructed user profile"; 2015 International Conference on Advances in Computing, Communications and Informatics (ICACCI), pp. 818-823; IEEE; 2015.

IBM; "Description, Enforcement and Presentation of Privacy Policies based on Contextual Integrity"; http://ip.com/IPCOM/000126489D Jul. 21, 2005.

Anonymously; "Determining Demographic User Information Based on Limited Initial User Data"; http://ip.com/IPCOM/000228909D; Jul. 11, 2013.

* cited by examiner

SYSTEM, METHOD, AND RECORDING MEDIUM FOR PREVENTING BACK PROPOGATION OF DATA PROTECTION

BACKGROUND

The present invention relates generally to a data protection system, and more particularly, but not by way of limitation, to a method, system, and third-party intermediary for a trusted, secure, and private transfer of data between two parties that can identify that correct content has been delivered but without a back propagation of private information between the two parties.

Twenty percent of the American population is estimated to have a recognized disability and many others have cognitive limitations that require special assistance or a modified interface when using some of the most basic necessities in today's society. These persons require web-based content that has been reduced in complexity in terms of sentence structures, word selection, and sentence length or otherwise adapted to assist their use of the web-based content. Beyond certain classifiable disabilities, persons may also have other visual problems like cataracts, growing deafness, or loss of fine motor skills to operate a computer mouse or the like. Adjustments are required for all their web-based interactions with government (Social Security, Medicare, Health Care Exchange, etc.), financial institutions (banks, 401K investments), health insurance companies, and health care providers and may have significant and growing physical, mental, and cognitive limitations.

Due to the necessity of an adapted interface or the like when using web-based services, conventional techniques have considered storing user preferences and limitations in a central cloud infrastructure (i.e., a library of personal profiles or the like). The conventional techniques have proposed to provide the institution providing the web-based service with the user profiles and then the institution will know the disability of the user and provide the user with an appropriate modified interface to utilize the web-based service. That is, the conventional techniques employ a user-to-user exchange of data. As a result, personal information must be disclosed to use the web-based services.

Thus, the conventional techniques have a technical problem in that the conventional techniques require disclosure of disabilities to an institution in order for the institution to provide a modified web-based service adapted to be accessible even with the disabilities of the user. The personal profile being accessible by institutions may not only violate laws, but there is significant user concern about having one central organization with access to physical limitations. Access to cognitive capabilities, especially declining cognitive capabilities of the aging, may be an even larger concern than physical limitations.

SUMMARY

In one aspect of the invention and in view of the above drawbacks of the conventional techniques, the inventors have considered a technical solution to the technical problem by providing a third party intermediary and a data protection system capable of securing disability information about a user and preventing an institution providing a web-based service from identifying the disability of the user while allowing the institution to provide a plurality of interfaces to be matched with the user based on the disability input. That is, the present invention allows the institution to receive the required data from the web-based service without receiving any disability information of the user and matching the user to an appropriately modified web-based service.

In an exemplary embodiment, the present invention can provide a data protection system, including a content request receiving circuit configured to receive a service request from a user, to communicate the service request to a provider, and to receive pre-approved versions of content from the provider, a content matching circuit configured to match a pre-approved version of content of the pre-approved versions of content to the user based on a condition of the user, a user data receiving circuit configured to receive user data to complete the pre-approved version of the content, and a zero-knowledge verifiable computing circuit configured to execute a program using zero-knowledge verifiable computing to remove private content from the pre-approved version of the content to ensure privacy of the condition of the user from the provider.

Further, in another exemplary embodiment, the present invention can provide a data protection method, including receiving a service request from a user and receiving pre-approved versions of content from a provider, matching a pre-approved version of content of the pre-approved versions of content to the user based on a condition of the user, receiving user data to complete the pre-approved version of the content, and executing a program using zero-knowledge verifiable computing to remove private content from the pre-approved version of the content to ensure privacy of the condition of the user from the provider.

Even further, in another exemplary embodiment, the present invention can provide a third party intermediary for exchanging private data between a user and a provider, the third party intermediary including a content matching circuit configured to match a pre-approved version of content of pre-approved versions of content to the user based on a condition of the user and to send the matched pre-approved version of content to a first device for the user to complete the matched pre-approved version of content, and a zero-knowledge verifiable computing circuit configured to execute a program using zero-knowledge verifiable computing to remove private content from the pre-approved version of the content completed by the user to ensure privacy of the condition of the user from the provider.

There has thus been outlined, rather broadly, an embodiment of the invention in order that the detailed description thereof herein may be better understood, and in order that the present contribution to the art may be better appreciated. There are, of course, additional exemplary embodiments of the invention that will be described below and which will form the subject matter of the claims appended hereto.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

The exemplary aspects of the invention will be better understood from the following detailed description of the exemplary embodiments of the invention with reference to the drawings.

DETAILED DESCRIPTION OF THE EXEMPLARY EMBODIMENTS

Figure 1:
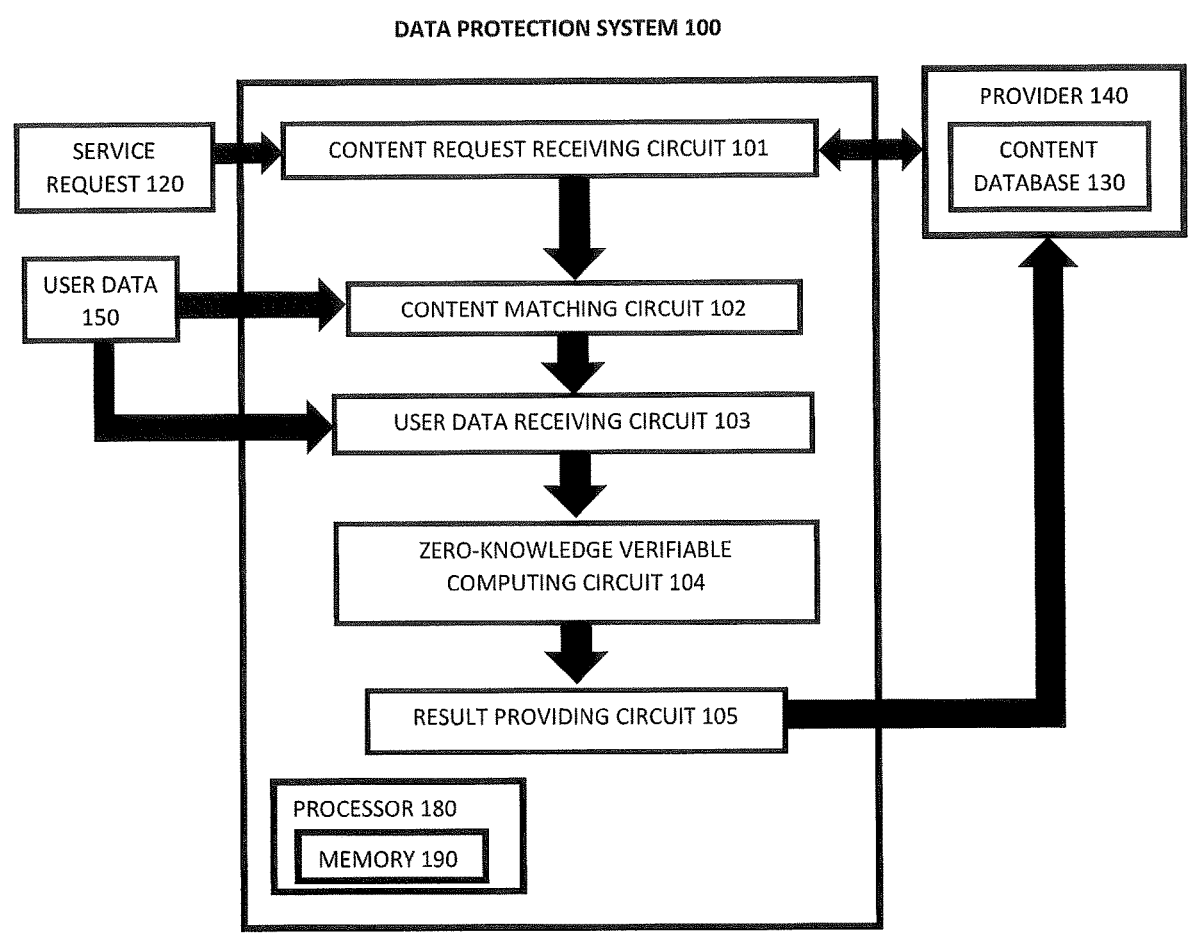
FIG. 1 exemplarily shows a block diagram illustrating a configuration of a data protection system 100.

The invention will now be described with reference to FIGS. 1-6, in which like reference numerals refer to like parts throughout. It is emphasized that, according to common practice, the various features of the drawing are not necessarily to scale. On the contrary, the dimensions of the various features can be arbitrarily expanded or reduced for clarity. Exemplary embodiments are provided below for illustration purposes and do not limit the claims.

With reference now to FIG. 1, the data protection system 100 includes a content request receiving circuit 101, a content matching circuit 102, a user data receiving circuit 103, a zero-knowledge verifiable computing circuit 104, and a result providing circuit 105. The data protection system 100 includes a processor 180 and a memory 190, with the memory 190 storing instructions to cause the processor 180 to execute each circuit of data protection system 100. The processor and memory may be physical hardware components, or a combination of hardware and software components.

Although the data protection system 100 includes various circuits, it should be noted that a data protection system can include modules in which the memory 190 stores instructions to cause the processor 180 to execute each module of data protection system 100.

Also, each circuit can be a stand-alone device, unit, module, etc. that can be interconnected to cooperatively produce a transformation of the data to a desired result.

With the use of these various circuits, the data protection system 100 may act in a more sophisticated and useful fashion, and in a cognitive manner while giving the impression of mental abilities and processes related to knowledge, attention, memory, judgment and evaluation, reasoning, and advanced computation. That is, a system is said to be "cognitive" if it possesses macro-scale properties—perception, goal-oriented behavior, learning/memory and action—that characterize systems (i.e., humans) that all agree are cognitive.

Cognitive states are defined as functions of measures of a user's total behavior collected over some period of time from at least one personal information collector (including musculoskeletal gestures, speech gestures, eye movements, internal physiological changes, measured by imaging circuits, microphones, physiological and/or kinematic sensors in a high dimensional measurement space) within a lower dimensional feature space. In one exemplary embodiment, certain feature extraction techniques are used for identifying certain cognitive and emotional traits. Specifically, the reduction of a set of behavioral measures over some period of time to a set of feature nodes and vectors, corresponding to the behavioral measures' representations in the lower dimensional feature space, is used to identify the emergence of certain cognitive state(s) over that period of time. One or more exemplary embodiments use certain feature extraction techniques for identifying certain cognitive states. The relationship of one feature node to other similar nodes through edges in a graph corresponds to the temporal order of transitions from one set of measures and the feature nodes and vectors to another. Some connected subgraphs of the feature nodes are herein also defined as a cognitive state. The present application also describes the analysis, categorization, and identification of these cognitive states by further feature analysis of subgraphs, including dimensionality reduction of the subgraphs, for example by graphical analysis, which extracts topological features and categorizes the resultant subgraph and its associated feature nodes and edges within a subgraph feature space.

Figure 4:
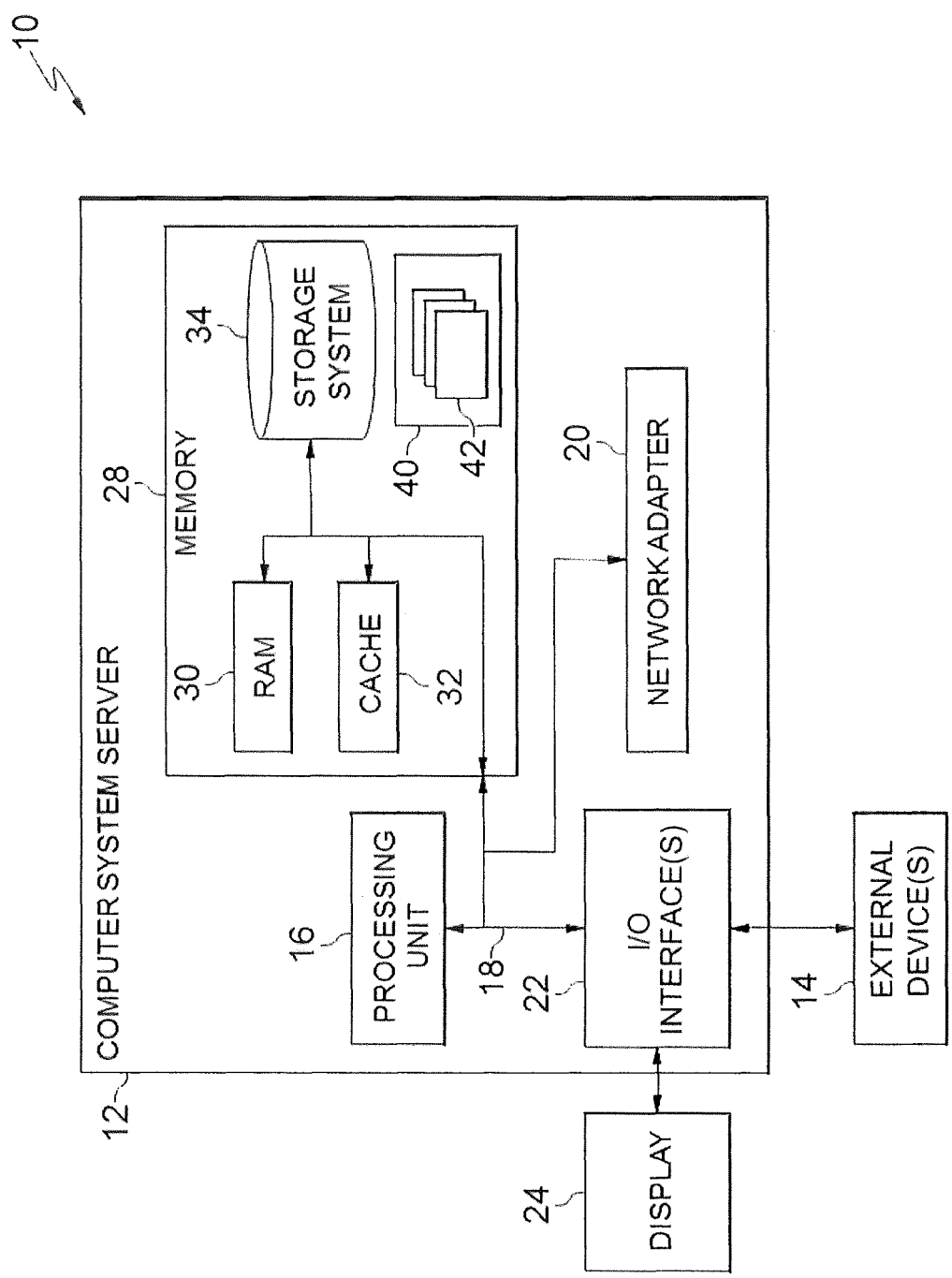
FIG. 4 depicts a cloud computing node 10 according to an embodiment of the present invention.
Figure 5:
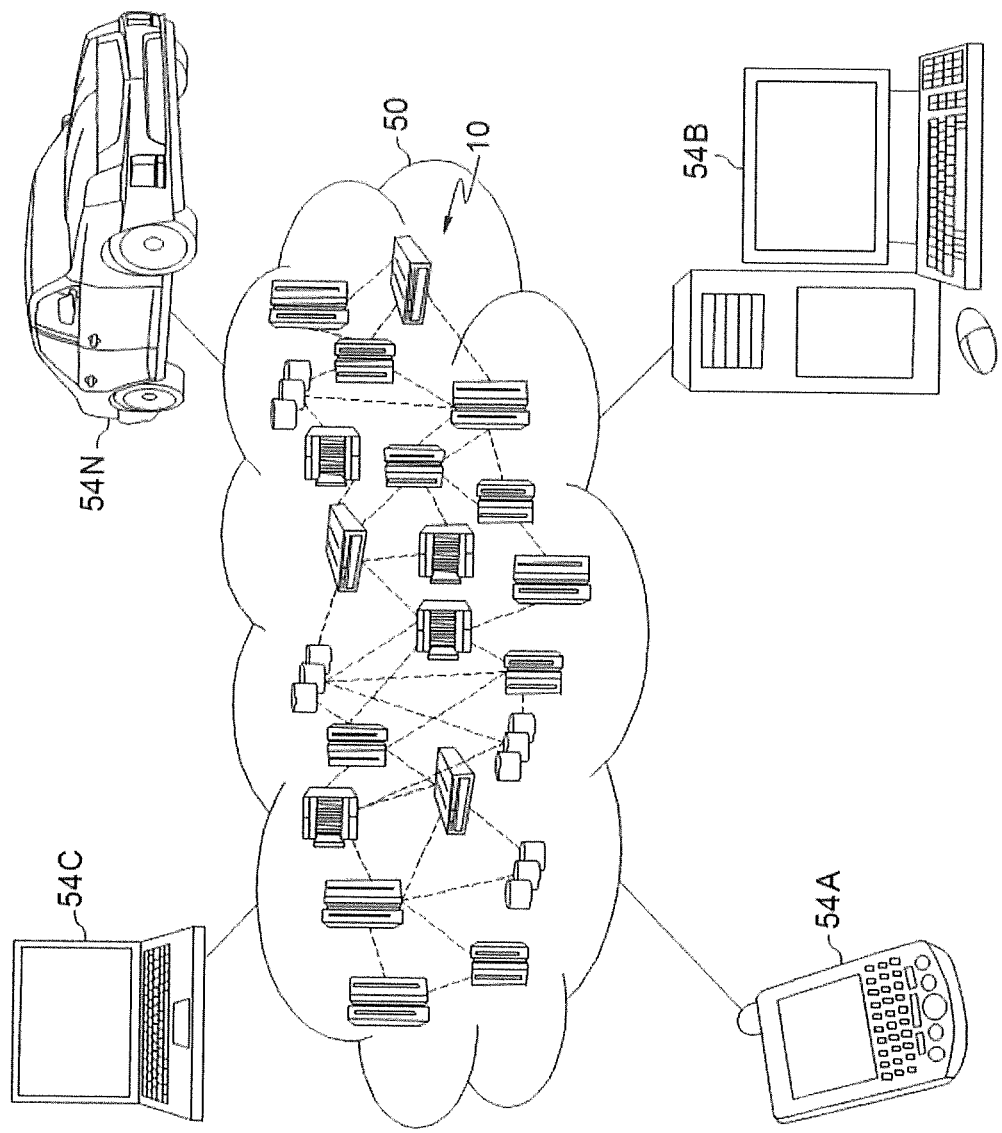
FIG. 5 depicts a cloud computing environment 50 according to another embodiment of the present invention.
Figure 6:
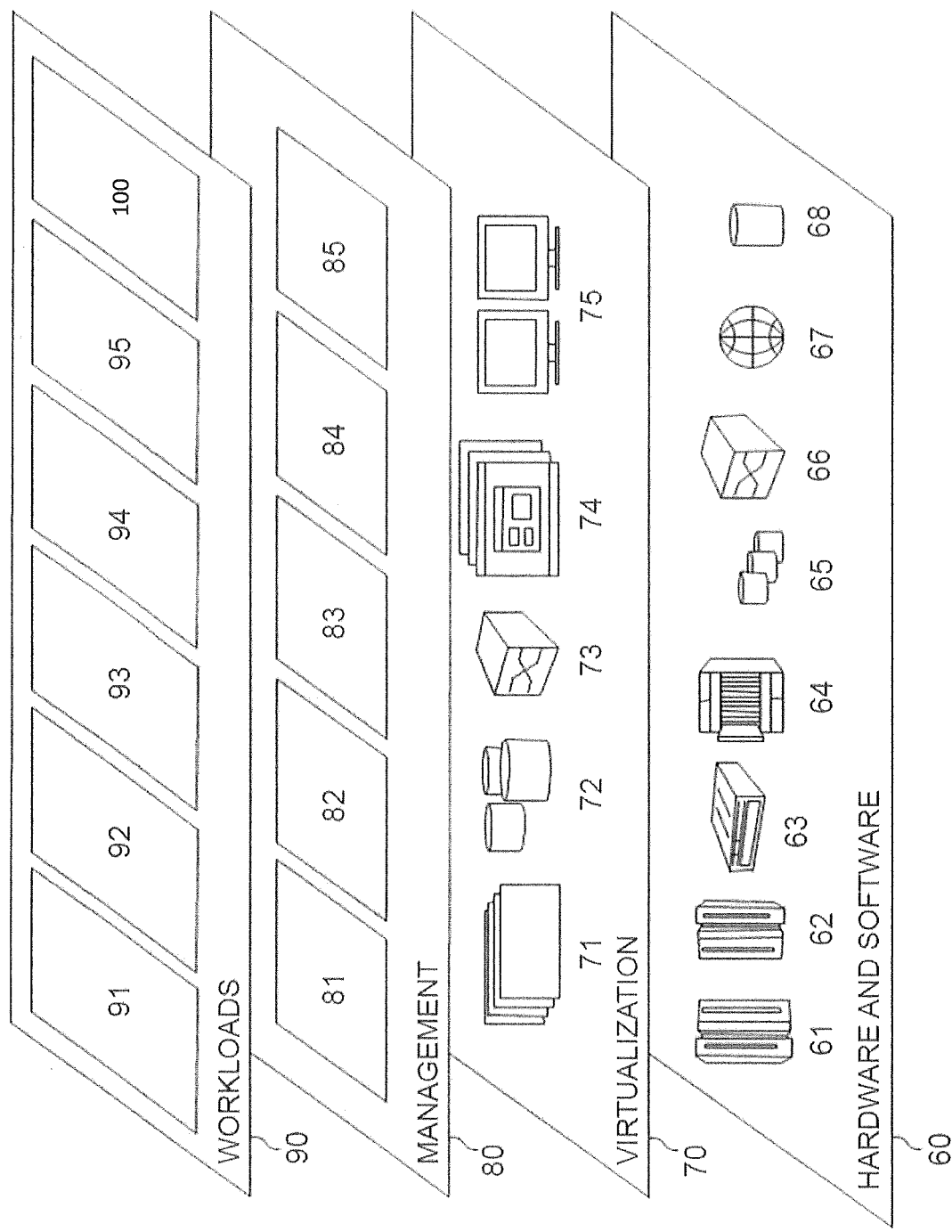
FIG. 6 depicts abstraction model layers according to an embodiment of the present invention.

Although as shown in FIGS. 4-6 and as described later, the computer system/server 12 is exemplarily shown in cloud computing node 10 as a general-purpose computing circuit which may execute in a layer the data protection system 100 (FIG. 6), it is noted that the present invention can be implemented outside of the cloud environment.

The content request receiving circuit 101 receives a service request 120 from a user. That is, the service request 120 is a request to access a website, digital form, or the like from a provider 140 such as a bank, government, health insurance provider or the like. The content request receiving circuit 101 outputs to the provider that the service request 120 has been received. The provider 140 sends pre-approved versions of all possible content stored in a content database 130 that the user will fill out to the content request receiving circuit 101.

For example, the pre-approved versions of content can include different cognitive levels, alternate color schemes, alternate diagrams, and pictures, audio or textual content. Thus, each pre-approved version of the content can provide a more suitable form to fill out for a person with a disability. That is, the pre-approved versions of the content provides users with physical, mental, or cognitive limitations Internet content that has been personalized to allow them to successful navigate and interact with online content. The providers 140 of on-line services like banks, insurance companies, investment firms, and government pre-approve all content that is displayed to users. These reviews and approvals would include legal, marketing, brand management, and accessibility review groups. The content does not need to be pre-approved but pre-approved content is preferred.

In addition to the service request 120 sent by the user, the user inputs user data 150 to the content matching circuit 102 and the user data receiving circuit 103. First, the content matching circuit 102 analyzes the user data 150 to identify the disability of the user or the private information that the user does not want to communicate to the provider 140. The content matching circuit 102 matches a pre-approved version of the content out of the pre-approved versions of the content with the specific disability of the user such that the user can fill out the form.

Users do not want to surrender their personal data about limitations to vital online services as the price to access on-line services. For example, a user with a mental handicap may need a modified content in order to be able to utilize the on-line services. However, the user does not want the providers 140 to know of their disability such that the disability can be public and potentially be used against the user.

Therefore, the content matching circuit 102 matches the pre-approved versions of the content based on the disability of the user without informing the providers 140 which version is being provided to the user.

The user data receiving circuit 103 receives the user data 150 required to complete the pre-approved version of the content.

The user data receiving circuit 103 outputs the completed pre-approved version of content to the zero-knowledge verifiable computing circuit 104. The zero-knowledge verifiable computing circuit 104 executes a program using zero-knowledge verifiable computing to remove all of the private content from the user data 150 input into the pre-approved version of the content. The program using the zero-knowledge verifiable computing is based on combinatorial logic with the one or more inputs using a zero-knowledge protocol to ensure privacy of the user from the provider 140. That is, no personal information about the user is conveyed to the provider other than the required information to complete the transaction because of the zero-knowledge verifiable computing circuit 104 and only the proof that the program which checks the predefined conditions or the appropriateness of a particular medical treatment has run successfully and without modification will be provided to the provider 140 by the result providing circuit 105. Therefore, the result providing circuit 105 can provide the needed data to the provider 140 to complete the request without providing any personal information of the user by way of the zero-knowledge verifiable computing circuit 104.

The result providing circuit 105 provides the provider 140 and the user an output of the combinational logic along with proof from the zero-knowledge protocol that the combinatorial logic was executed without alteration or display of the personal information.

It is noted that the service request 120 includes one or more inputs to perform a stateless transaction based on combinational logic, an output of the combinational logic is a function of only the one or more inputs. The stateless transaction based one the combinational logic is one of a set of a plurality of stateless transactions using zero-knowledge verifiable computing. The stateless transaction based on combinational logic can be on of an inequality function, a Boolean function, a RESTful application programming interface (API) or the like.

Further, the zero-knowledge verifiable computing of the zero-knowledge verifiable computing circuit 104 can be performed by various techniques. For example, the zero-knowledge verifiable computing can be a succinct computational integrity and privacy (SCIP) technique, a zero-knowledge succinct non-interactive argument of knowledge (zk-snark) technique, a probabilistically checkable proof (PCP) technique, or the like. In other words, the zero-knowledge verifiable computing circuit 104 uses a technique that is able to ensure the privacy of the user data from the party receiving it.

Also, the result providing circuit 105 provides the proof of the secured transaction including whether the program is using at least one of trusted computing, secure boot attestation, or a combination thereof.

Figure 2:
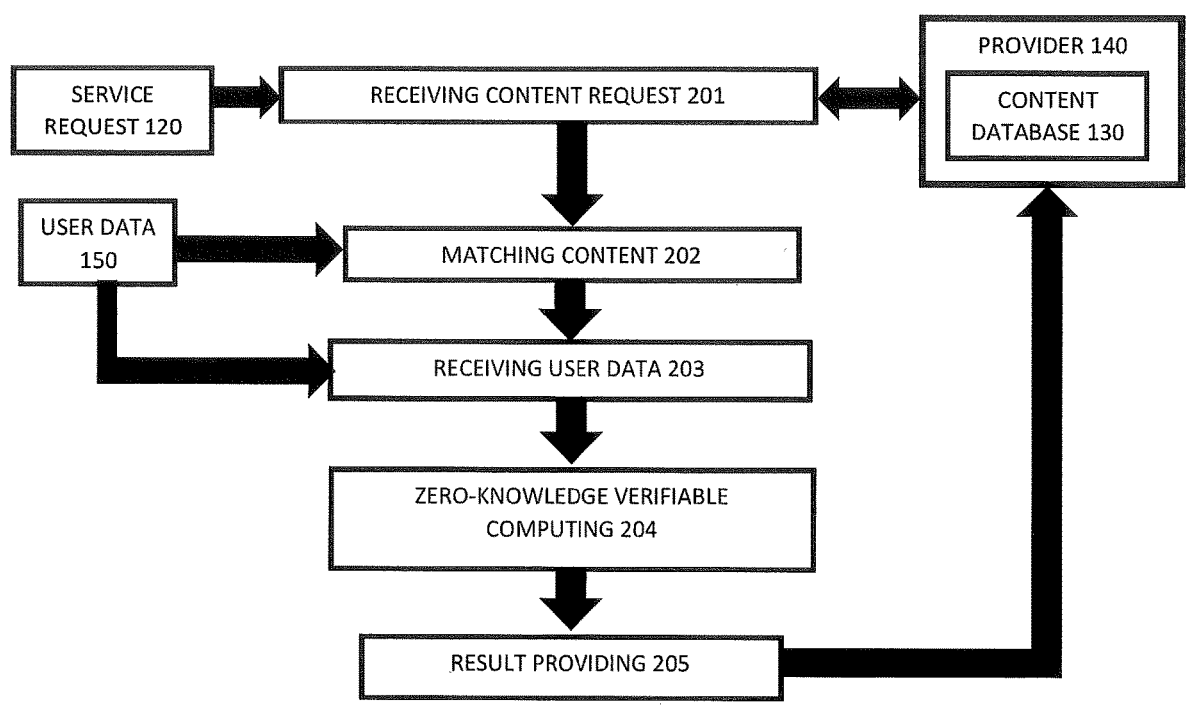
FIG. 2 exemplarily shows a high level flow chart for a data protection method 200.

FIG. 2 shows a high level flow chart for a method 200 of data protection receiving data 120.

Step 201 receives a service request 120 from a user and communicates the service request to a provider 140. Step 201 further receives pre-approved versions of all possible content stored in a content database 130 of the provider 140 that the user will fill out. It is noted that the service request 120 may be sent directly to the provider 140 and the pre-approved versions of all possible content are sent directly to Step 202.

Step 202 receives the pre-approved versions of all possible content and the user data 150.

Step 202 receives the data 120 and analyzes a context of the user based on the data 120 and matches the pre-approved versions of the content based on the disability of the user without informing the providers 140 which version is being provided to the user.

Step 203 receives the user data from the user after the pre-approved version of the content matched to the user has been filled out.

Step 204 executes a program using zero-knowledge verifiable computing to remove all of the private content from the user data 150 input into the pre-approved version of the content.

Step 205 provides the results of Step 204 to the provider 140 and the user with the output of the combinational logic along with proof from the zero-knowledge protocol that the combinatorial logic was executed without alteration or display of the personal information by Step 204.

Figure 3:
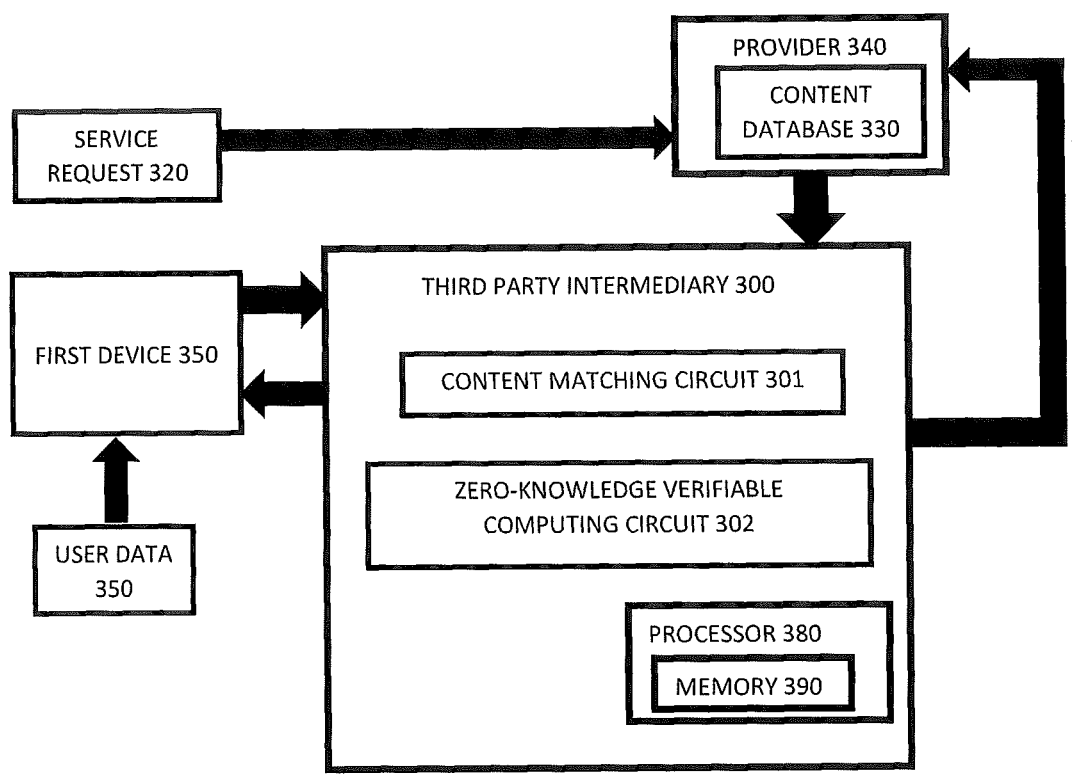
FIG. 3 exemplarily shows a block diagram illustration a configuration of a third party intermediary 300.

FIG. 3 exemplarily shows a third party intermediary 300 including a content matching circuit 301 and a zero-knowledge verifiable computing circuit 302. The third party intermediary 300 includes a processor 380 and a memory 390, with the memory 390 storing instructions to cause the processor 380 to execute each circuit of the third party intermediary 300. The processor and memory may be physical hardware components, or a combination of hardware and software components.

Although the third party intermediary 300 includes various circuits, it should be noted that a data protection system can include modules in which the memory 390 stores instructions to cause the processor 380 to execute each module of third party intermediary 300.

Also, each circuit can be a stand-alone device, unit, module, etc. that can be interconnected to cooperatively produce a transformation of the data to a desired result.

The third party intermediary 300 is a third party for exchanging data between a user and a provider 340.

The third party intermediary 300 receives pre-approved versions of all possible content stored in a content database 130 of the provider 140 based on a service request 320 of the user that the user will fill out on the first device 350.

After the third party intermediary 300 receives the pre-approved versions of all possible content, based on the user data 350 input into the first device 350, the content matching circuit 301 matches a specific version of the pre-approved versions of all possible content to the user based on a disability, cognitive limitation, mental limitation, or the like. That is, the third party intermediary 300 receives the disability of the user without communicating the disability of the user to the provider.

After the content matching circuit 301 matches the specific version of the pre-approved versions of all possible content to the user, the third party intermediary 300 outputs the specific version to the first device 350 such that the user can input the information into the specific version that has been adapted to satisfy their needs.

After the specific version is completed and output back to the third party intermediary 300, the zero-knowledge verifiable computing circuit 302 executes a program using zero-knowledge verifiable computing to remove all of the private content from the user data 150 input into the pre-approved version of the content.

The third party intermediary 300 provides the provider 140 and the user with the output of the combinational logic along with proof from the zero-knowledge protocol that the combinatorial logic was executed without alteration or display of the personal information by the zero-knowledge verifiable computing circuit 302. Therefore, the provider 140 receives the information needed to complete the web-based transaction while the user is allowed to use a modified form adapted to help with their disability while not allowing the provider 140 to view the disability of the user.

As is evidenced by above, it is clear that the invention is so rooted in requiring a computer and is dependent upon the computer components to perform the invention. That is, the invention cannot be performed by a human using paper and pencil as the intermediary because giving a human access to the end user's personal physical, mental, or cognitive data defeats the entire design goal of preventing sharing of that data to other parties.

Also, it is clear that the invention improves the pre-existing technologies in the field in that conventionally personal user data regarding disabilities or the like was required by the provider 140 in order for the provider 140 to supply the user with a correct version of the content adapted to the user's disabilities. However, the present invention improves data security of individuals without compromising the individual's ability to use modified content adapted to their personal needs.

Further, the additional step of at least zero-knowledge verifiable computing to allow for transfer of data securely between a user and a second party is an unconventional step that enables the invention to be particularly useful in a growing Internet centric society.

Based on at least the above examples, it is clear that the invention provides significantly more than any abstract idea a person of ordinary skill might attempt to classify the invention as.

Exemplary Hardware Aspects, Using a Cloud Computing Environment

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client circuits through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (Paas): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 4, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10, there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop circuits, multiprocessor systems, microprocessor-based systems, set top boxes, programmable consumer electronics, network PCs, minicomputer systems, mainframe computer systems, and distributed cloud computing environments that include any of the above systems or circuits, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing circuits that are linked through a communications network. In a distributed cloud computing environment, program modules may be located in both local and remote computer system storage media including memory storage circuits.

As shown in FIG. 4, computer system/server 12 in cloud computing node 10 is shown in the form of a general-purpose computing circuit. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external circuits 14 such as a keyboard, a pointing circuit, a display 24, etc.; one or more circuits that enable a user to interact with computer system/server 12; and/or any circuits (e.g., network card, modem, etc.) that enable computer system/server 12 to communicate with one or more other computing circuits. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, circuit drivers, redundant processing units, external disk drive arrays, RAID systems, tape drives, and data archival storage systems, etc.

Referring now to FIG. 5, illustrative cloud computing environment 50 is depicted. As shown, cloud computing environment 50 comprises one or more cloud computing nodes 10 with which local computing circuits used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing circuit. It is understood that the types of computing circuits 54A-N shown in FIG. 8 are intended to be illustrative only and that computing nodes 10 and cloud computing environment 50 can communicate with any type of computerized circuit over any type of network and/or network addressable connection (e.g., using a web browser).

Referring now to FIG. 6, a set of functional abstraction layers provided by cloud computing environment 50 (FIG.

5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage circuits 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, more particularly relative to the present invention, the data protection system 100 described herein.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A data protection system, comprising:
    a content request receiving circuit configured to receive a service request from a user, to communicate the service request to a provider, and to receive pre-approved versions of content from the provider;
    a content matching circuit configured to match a pre-approved version of content of the pre-approved versions of content to the user based on a condition of the user;
    a user data receiving circuit configured to receive user data to complete the pre-approved version of the content; and
    a zero-knowledge verifiable computing circuit configured to execute a program using zero-knowledge verifiable computing to remove private content from the pre-approved version of the content to ensure privacy of the condition of the user from the provider,
    wherein the user data is received via a third party intermediary that exchanges data between the user and the provider and that is separate from the user and the provider,
    wherein herein the zero-knowledge verifiable computing comprises a technique that is able to ensure the privacy of the user data from the party receiving it, and
    wherein the zero-knowledge verifiable computing circuit carries out the zero-knowledge verifiable computing based on combinatorial logic with the completed pre-approved version of the content using a zero-knowledge protocol.

2. The system of claim 1, further comprising a result providing circuit configured to provide the pre-approved version of the content with the private content removed, to the provider.

3. The system of claim 1, wherein the zero-knowledge verifiable computing circuit performs the zero-knowledge verifiable computing using combinatorial logic with the pre-approved version of the content using a zero-knowledge protocol to ensure privacy of the condition of the user from the provider.

4. The system of claim 1, further comprising a result providing circuit configured to provide an output of combinational logic used in the zero-knowledge verifiable computing along with proof from the zero-knowledge protocol that the combinational logic was executed without alteration.

5. The system of claim 1, wherein the provider receives a completed version of content matched to the user devoid of the condition of the user.

6. The system of claim 1, wherein the zero-knowledge verifiable computing comprises a succinct computational integrity and privacy (SCIP) technique.

7. The system of claim 1, wherein the zero-knowledge verifiable computing comprises a zero-knowledge succinct non-interactive argument of knowledge (zk-snark) technique.

8. The system of claim 1, wherein the zero-knowledge verifiable computing comprises a probabilistically checkable proof (PCP) technique.

9. The system of claim 4, wherein the proof includes whether the program is using at least one of trusted computing, secure boot attestation, or a combination thereof.

10. The system of claim 1, wherein the provider directly receives the service request, and
    wherein the content request receiving circuit receives the pre-approved versions of content from the provider, from the provider.

11. A data protection method, comprising:
receiving a service request from a user and receiving pre-approved versions of content from a provider;
matching a pre-approved version of content of the pre-approved versions of content to the user based on a condition of the user;
receiving user data to complete the pre-approved version of the content; and
executing a program using zero-knowledge verifiable computing to remove private content from the pre-approved version of the content to ensure privacy of the condition of the user from the provider,
wherein the user data is received via a third party intermediary that exchanges data between the user and the provider and that is separate from the user and the provider,
wherein herein the zero-knowledge verifiable computing comprises a technique that is able to ensure the privacy of the user data from the party receiving it, and
wherein the zero-knowledge verifiable computing circuit carries out the zero-knowledge verifiable computing based on combinatorial logic with the completed pre-approved version of the content using a zero-knowledge protocol.

12. The method of claim 11, further comprising providing the pre-approved version of the content with the private content removed, to the provider.

13. The method of claim 11, wherein executing the program performs the zero-knowledge verifiable computing using combinatorial logic with the pre-approved version of the content using a zero-knowledge protocol to ensure privacy of the condition of the user from the provider.

14. The method of claim 11, further comprising providing an output of combinational logic used in the zero-knowledge verifiable computing along with proof that the combinational logic was executed without alteration.

15. A data protection system for exchanging private data between a user and a provider, the system comprising:
a content matching circuit configured to match a pre-approved version of content of pre-approved versions of content to the user based on a condition of the user, and to send the matched pre-approved version of content to a first device for the user to complete the matched pre-approved version of content; and
a zero-knowledge verifiable computing circuit configured to execute a program using zero-knowledge verifiable computing to remove private content from the pre-approved version of the content completed by the user, to ensure privacy of the condition of the user from the provider,
wherein the user data is received via a third party intermediary that exchanges data between the user and the provider and that is separate from the user and the provider,
wherein herein the zero-knowledge verifiable computing comprises a technique that is able to ensure the privacy of the user data from the party receiving it, and
wherein the zero-knowledge verifiable computing circuit carries out the zero-knowledge verifiable computing based on combinatorial logic with the completed pre-approved version of the content using a zero-knowledge protocol.

16. The system of claim 15, wherein the pre-approved versions of content are provided to the third party intermediary based on a service request by the user.

17. The system of claim 15, wherein the third party intermediary provides an output of combinational logic used in the zero-knowledge verifiable computing along with proof from the zero-knowledge protocol that the combinational logic was executed without alteration to the first device and to the provider.

18. The system of claim 15, wherein the third party intermediary communicates with the first device and the provider independently of each other such that the condition of the user is not accessed by the provider.

* * * * *